(12) United States Patent
Gillespie et al.

(10) Patent No.: US 6,500,866 B1
(45) Date of Patent: Dec. 31, 2002

(54) 1-(ADAMANTYL)AMIDINES AND THEIR USE IN THE TREATMENT OF CONDITIONS GENERALLY ASSOCIATED WITH ABNORMALITIES IN GLUTAMATERGIC TRANSMISSION

(75) Inventors: Roger John Gillespie, Wilts (GB); Michael Fredrick Snape, London (GB); Simon Edward Ward, Reading (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/581,340

(22) PCT Filed: Dec. 11, 1998

(86) PCT No.: PCT/GB98/03715

§ 371 (c)(1),
(2), (4) Date: Sep. 11, 2000

(87) PCT Pub. No.: WO99/31051

PCT Pub. Date: Jun. 24, 1999

(30) Foreign Application Priority Data

Dec. 12, 1997 (GB) .............................................. 9726388

(51) Int. Cl.$^7$ .............................................. A61K 31/155
(52) U.S. Cl. ........................................ 514/631; 564/225
(58) Field of Search ........................... 514/631; 564/225

(56) References Cited

U.S. PATENT DOCUMENTS

| 5,552,443 A | | 9/1996 | Keana et al. ................ 514/631 |
| 6,114,392 A | * | 9/2000 | Gilad et al. .................. 514/634 |

FOREIGN PATENT DOCUMENTS

| DE | 2 306 784 | 8/1973 |
| DE | 151 447 | 10/1981 |
| GB | 1 478 477 | 6/1977 |

OTHER PUBLICATIONS

CA:83:109072 abs of J Med Chem by Aigami et al 18(7) pp 713–721, 1975.*
CA:88:22333 abs DE2604196, Aug. 1977.*

* cited by examiner

Primary Examiner—Jean F. Vollano
(74) Attorney, Agent, or Firm—Foley & Lardner

(57) ABSTRACT

Compounds of 1-(adamantyl) amidine and their use in the treatment of conditions generally associated with abnormalities in glutamatergic transmittion.

20 Claims, No Drawings

1-(ADAMANTYL)AMIDINES AND THEIR USE IN THE TREATMENT OF CONDITIONS GENERALLY ASSOCIATED WITH ABNORMALITIES IN GLUTAMATERGIC TRANSMISSION

This application is a 371 of PCT/GB98/03715 filed Dec. 11, 1998, now WO 99/31051.

The present invention relates to compounds and compositions for use in the treatment of conditions generally associated with abnormalities in glutamatergic transmission.

The excitatory neurotransmission underlying brain function is primarily (about 80 per cent) dependent on the action of glutamate and other related neurotransmitters on specific receptors activated by the excitatory amino acids. These receptors fall into several categories, one of which is the glutamate receptor specifically sensitive to the agonist N-methyl-D-aspartate (the NMDA receptor). NMDA receptor subtypes are ubiquitously expressed in mamnmalian brain and have unique properties underlying their role in synaptic function and plasticity. In view of the central role of these receptors in normal central nervous system function, numerous suggestions have been made as to the utility of drugs acting at this receptor to modulate the processes underlying various disease states. The NMDA receptor has been studied with particular interest in relation to its apparent involvement in the pathophysiology of neurodegenerative diseases.

Non-competitive antagonists at this receptor should be particularly advantageous in the treatment of diseases since such compounds would have activity that should not be overcome by high levels of endogenous agonists and would act equally well independent of the endogenous agonist activating the receptor. This is important since high levels of endogenous glutamate can occur in certain pathological processes and there are a variety of different endogenous agonists that can act through a variety of specific modulatory agonist binding sites on the receptor.

A number of NMDA antagonists have been disclosed which operate by binding to the ion-channel of the NMDA receptor. The advantage of channel blockers is that they operate only on the "open" channel and therefore do not affect unactivated receptors. In addition they are effective regardless of the mechanism of receptor stimulation and their effect will not be diminished by large concentrations of endogenous agonist.

Given that the NMDA receptor plays a primary role in normal central nervous system function, it is not surprising that certain drugs acting to block or antagonise the function of this receptor affect normal function within the brain. This may be manifested as central nervous system side effects such as hallucinations, confusion, paranoia, aggression, agitation and catatonia. These side effects can be described as a psychotic state and the drugs that induce them are known as psychotomimetic NMDA antagonists. Such side effects limit the utility of these compounds in treating disease states. NMA receptor antagonists that have efficacy in treating central nervous system disorders but without such psychotomimetic side effects would have a clear therapeutic advantage. Thus, in view of the crucial role played by the NMDA receptor in either the progression or expression of the disease pathology and process, it is an object of this invention to provide compounds for the treatment of central nervous system disorders which modulate the activity of the NMDA receptor but which are well-tolerated in the sense of having a markedly reduced propensity to induce psychotomimetic side effects.

The present invention is particularly concerned with the treatment of neurodegenerative disorders. There is a large body of evidence to suggest that either an excitotoxic or slow excitotoxic pathological over-activation of the NMDA receptor induces the death of neurons in a variety of disorders such as ischaemic stroke, other forms of hypoxic injury, haemorrhagic brain injury, traumatic brain injury, Alzheimer's disease, Parkinson's disease, Huntington's disease and other dementing diseases. There is thus clear evidence that antagonism of the NMDA receptor will reduce or prevent the neurodegeneration that underlies the disease process in these and related conditions. There is also evidence to suggest that a well tolerated compound will allow effective symptomatic treatment of the manifestations of the disease process in these disorders as well as reducing the primary underlying neurodegeneration process. Also, it is known that disorders previously described as involving acute neurodegeneration have longer than expected elevations in glutamate release and consequently require longer than expected treatment with NMDA antagonists. There would therefore be a therapeutic advantage for new drugs which are well tolerated and which can therefore be administered chronically.

The published literature contains references to a number of compounds and classes of compounds purported to be useful as NMDA antagonists.

The compounds Amantadine and Memantine and related anti-viral agents have been known for many years.

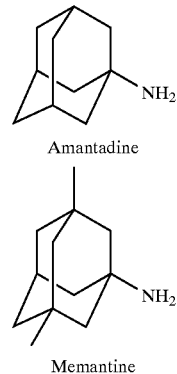

Amantadine

Memantine

Patent applications have been filed directed to the use of Memantine in the treatment of Parkiinson's Disease in the 1970s and as an NMDA antagonist in 1990 (see EP-A-0392059 and U.S. Pat. No. 5,061,703). Furthermore, International Patent application WO94/05275 proposes the use of Amantadine and related compounds such as Memantine in the treatment and prevention of non-ischaemic, long term NMDA receptor-mediated neuronal degeneration. An increase in affinity for the NMDA receptor due to substitution of the adamantane ring of Memantine with alkyl groups was noted and published by Komthuber et al., Eur. J. Pharmacol., 1991, 206, 297–300, by Kroemer et al., J. Med. Chem., 1998, 41, 393–400 and by Parsons et al., Neuropharmacology, 1995, 34, 1239–1258.

1-(Adamantyl)amidines are disclosed as antivirals in DE-A-2306784, JP-A-7391049, DD-A-151447 and GB-1478477. 1-(Adamantyl)acetamidine is disclosed in JP-A-120683 and GB-1478477. 1-(Adamantyl)amidrazones are disclosed as insecticides and acaricides in EP-A-0604798. N-substituted-1-(adamantyl)amidines are disclosed by May et al., Arzneim. Forsch., 1978, 28, 732–735, and the virostatic activities of the compounds reported. N-substituted-1-(adamantyl)amidines as antivirals are disclosed by Skwarski et al., Acta. Pol. Pharm., 1988, 45, 395–399.

The antiviral activities of adainantane derivatives including 1-(adamantyl)carbamidine and 1-(adamantyl)acetamidine are reported by Inamoto et al., J. Med. Chem., 1975, 18, 713–721, where they are compared with Amantadine.

As discussed above, psychotomimetic side-effects are observed during the use of a number of well known NMDA channel blockers and therefore it will be a considerable advantage to identify clinically well-tolerated antagonists where such side effects are minimised. Porter and Greenamyre (J. Neurochem. 1995, 64, 614–623; incorporated herein by reference) demonstrated that well tolerated and psychotomimnetic NMDA receptor channel blockers could be differentiated on the basis of their relative affinities for forebrain and cerebellar receptors irrespective of absolute affinities. Selectivity for cerebellar NMDA receptors over forebrain NMDA receptors is observed for well-tolerated compounds. The basis of this observation may be related to different populations of NMDA receptor subtypes in these brain regions.

The use of a number of the known NOMA antagonists such as Dizocilpine, PCP, Cerestat and Ketamine gives rise to a number of side effects which render these compounds unsuitable for use in treatment. In particular, administration of the compounds is associated with perceptual and cognitive disturbances of a kind that resemble naturally-occurring psychotic states.

In addition, the perceptual and cognitive side effects of the compounds become more pronounced after the onset of puberty and sexual maturation, and these compounds are therefore particularly unsuitable for the treatment of adults. This developmental change has been demonstrated empirically in both experimental animals and in man, and is paralleled in experimental animals by brain hypermetabolism.

In summary, there is a need for an NMDA antagonist which is well tolerated and does not give rise to the side effects associated with previous clinically investigated NMDA antagonists.

A number of compounds have now been found that show affinity for the NMDA receptor and are useful in the treatment of conditions generally associated with abnormalities in glutamatergic transmission such as stroke, traumatic brain injury and neurodegenerative diseases such as Parkinson's and Alzheimer's diseases. It has also been found that the compounds have a surprisingly favourable ratio of cortex to cerebellar binding affinity which indicates that these compounds should be well tolerated in vivo.

According to the present invention there is provided use of a compound of the formula (1):

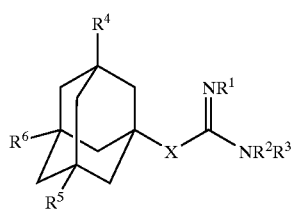

(1)

wherein
X is an allylene chain comprising 0, 1, 2, 3 or 4 carbon atoms;
$R^1$, $R^2$ and $R^3$ are independently selected from hydrogen, alkyl and aryl;
$R^4$, $R^5$ and $R^6$ are independently selected from hydrogen, alkyl, aryl, halogen and alkoxy;

and prodrugs thereof and pharmaceutically acceptable salts thereof;
in the manufacture of a medicament for use in the treatment of a condition generally associated with abnormalities in glutamatergic transmission.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl or propyl, more preferably methyl or ethyl.

As used herein, the term "aryl" means an aromatic group, such as phenyl or naphthyl, or a heteroaromatic group containing one or more, preferably one, heteratom, such as pyridyl, pyrrolyl, furanyl and thiophenyl. Preferably, the aryl group comprises phenyl.

The alkyl and aryl groups may be substituted or unsubstituted, preferably unsubstituted. Where substituted, there will generally be 1 to 3 substituents present, preferably 1 substituent. Substituents may include:-
carbon containing groups such as
 alkyl,
 aryl, arylalkyl; (e.g. substituted and unsubstituted phenyl, substituted and unsubstituted benzyl)
halogen atoms and halogen containing groups such as
 haloalkyl (e.g. trifluoromethyl);
oxygen containing groups such as
 alcohols (e.g. hydroxy, hydroxyalkyl, (aryl)(hydroxy)alkyl),
 ethers (e.g. alkoxy, alkoxyalkyl, aryloxyalkyl), aldehydes (e.g. carboxaldehyde),
 ketones(e.g. alkylcarbonyl, alkylcarbonylalkyl, arylcarbonyl, arylalkylcarbonyl, arylcarbonylalkyl)
 acids (e.g. carboxy, carboxyalkyl),
 acid derivatives such as esters (e.g. alkoxycarbonyl, alkoxycarbonylalkyl, alkycarbonylyoxy, alkycarbonylyoxyalkyl)
 and amides (e.g. aminocarbonyl, mono- or dialkylaminocarbonyl, aminocarbonylalkyl, mono- or dialkylaminocarbonylalkyl, arylaminocarbonyl);
nitrogen containing groups such as
 amines (e.g. amino, mono- or dialkylamino, aminoalkyl, mono- or dialkylaminoalkyl),
 azides,
 nitriles (e.g. cyano, cyanoalkyl),
 nitro;
sulphur containing groups such as
 thiols, thioethers, suphoxides, and sulphones (e.g. alkylthio, alkylsulfinyl, alkylsufonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl)
and heterocyclic groups containing one or more, preferably one, heteroatom, (e.g. thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocounarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl).

As used herein, the term "alkoxy" means alkyl-O— and "alkoyl" means alkyl-CO—.

As used herein, the term "halogen" means a fluorine, chlorine, bromine or iodine radical, preferably a bromine or chlorine radical.

As used herein the term "conditions generally associated with abnormalities in glutamatergic transmission" primarily includes ischaemic stroke, haemorrhagic stroke, subarrachnoid haemorrhage, subdural haematoma, coronary artery bypass surgery, neurosurgery, traumatic brain injury, traumatic spinal injury, Alzheimer's disease, Parkinson's disease, Huntington's disease, Pick's disease, Lewy body disease, senile dementia, spongiform encephalopathies, prion-protein induced neurotoxicity, peri-natal asphyxia, demyelinating disease, multiinfarct dementia, dementia pugilans, drug dependence, alcohol withdrawal, opiate withdrawal, motor neurone disease, multiple sclerosis, acute and chronic pain including neuropathic pain, cancer pain, trigeminal neuralgia, migraine, primary and secondary hyperalgesia, inflammatory pain, nociceptive pain, tabes dorsalis, phantom limb pain, spinal cord injury pain, central pain, post-herpetic pain, HIV pain and diabetic neuropathy. In addition, the term also includes the following conditions: epilepsy, multiple system atrophy, progressive supra-nuclear palsy, Friedrich's ataxia, autism, fragile X syndrome, tuberous sclerosis, attention deficit disorder, olivio-pontocerebellar atrophy, cerebral palsy, drug-induced optic neuritis, peripheral neuropathy, myelopathy, ischaemic retinopathy, glaucoma, cardiac arrest, encephalitis, depression, bi-polar disorder, schizophrenia, psychosis, behaviour disorders, impulse control disorders, pre-eclampsia, neuroleptic malignant syndrome, chronic fatigue syndrome, anorexia nervosa, anxiety disorders, generalised anxiety disorder, panic disorder, phobias, fresh water drowning and decompression.

As used herein, the term "pharmaceutically acceptable salt" means any pharmaceutically acceptable salt of the compound of formula (1). Salts may be prepared from pharmaceutically acceptable non-toxic acids including inorganic and organic acids. Such acids include acetic, benzenesulfonic, benzoic, camphorsulfonic, citric, dichloroacetic, ethenesulfonic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

The compounds of formula (1) may exist in a number of diastereomeric and/or enantiomeric forms. Reference in the present specification to "a compound of formula (1)" is a reference to all stereoisomeric forms of the compound and includes a reference to the unseparated stereoisomers in a mixture, racemic or non-racemic, and to each stereoisomer in its pure form.

The compounds of the present invention are active as NMDA antagonists and are well tolerated in that side effects are minimised. Experimental data are shown in Table 1.

In the compound of formula (1), preferably X is an alkylene chain comprising 0, 1 or 2 carbon atoms, more preferably 0 carbon atoms, in the chain.

In one embodiment of the invention, in the compound of formula (1), where X is an alkylene chain comprising 1, 2, 3 or 4 carbon atoms, one or more of the carbon atom(s) in the chain X may be independently substituted by substituent group(s) selected from alkyl and aryl. Where substituted, a carbon atom may have one or two substituents, preferably one. Preferred substituent groups are selected from methyl, ethyl, phenyl and benzyl, preferably ethyl and benzyl. Where X is substituted, it is preferred that only one carbon atom in the chain is substituted.

In an alternative embodiment of the invention, in the compound of formula (1), X is unsubstituted and has the formula $(CH_2)_n$ where n=0 to 4, preferably n=0, 1 or 2 and more preferably n=0.

In the compound of formula (1), preferably $R^1$ and $R^2$ are hydrogen and $R^3$ is selected from hydrogen, alkyl and aryl. In a preferred embodiment, $R^1$, $R^2$ and $R^3$ are hydrogen.

In the compound of formula (1), preferably at least one of $R^4$, $R^5$ and $R^6$ is alkyl, aryl, halogen or alkoxy. Preferably $R^4$ is selected from hydrogen, alkyl and halogen, more preferably alkyl and more preferably methyl. Preferably $R^5$ is selected from hydrogen and alkyl, preferably hydrogen and methyl. Preferably $R^6$ is selected from hydrogen and alkyl, preferably hydrogen and methyl.

In a preferred embodiment, the compound of formula (1) is a compound where X has 1 carbon atom (i.e. n=1) and is unsubstituted; $R^1$, $R^2$ and $R^3$ are hydrogen; $R^4$ and $R^5$ are methyl; and $R^6$ is hydrogen.

In a further preferred embodiment, the compound of formula (1) is a compound where X has one carbon atom (i.e. n=1) and is substituted by an ethyl or benzyl group; and $R^1$, $R^2$, $R^3$, $R^4$, $R^5$ and $R^6$ are hydrogen.

In a particularly preferred embodiment, the compound of formula (1) is a compound of formula (1) where X has 0 carbon atoms (i.e. n=0); $R^1$, $R^2$ and $R^3$ are hydrogen; $R^4$ and $R^5$ are $CH_3$; and $R^6$ is hydrogen.

In a further particularly preferred embodiment, the compound of formula (1) is a compound where X has 0 carbon atoms (i.e., n=0); $R^1$, $R^2$ and $R^3$ are hydrogen; $R^4$ is methyl; and $R^5=R^6=$hydrogen or methyl.

The present invention further provides a method of treatment of conditions generally associated with abnormalities in glutamatergic transmission comprising administering to a patient an effective dose of a compound of formula (1) as defined above.

The present invention also provides a compound per se of the formula (1) as defined above wherein at least one of $R^4$, $R^5$ and $R^6$ is alkyl, aryl, halogen or alkoxy, with the proviso that if $R^1$, $R^2$ and $R^3$ are hydrogen and $R^4$, $R^5$ and $R^6$ are independently selected from hydrogen and $C_{1-4}$ alkyl, then either X is an alkylene chain of 2–4 carbon atoms, substituted or unsubstituted, as defined above, or X is an alkylene chain of 1 carbon atom substituted with one or two, preferably one, substituent group(s) independently selected from alkyl and aryl, and prodrugs and pharmaceutically acceptable salts thereof.

The present invention also provides a compound per se of the formula (1) as defined above wherein $R^4$, $R^5$ and $R^6$ are hydrogen and either X is an alkylene chain of 2–4 carbon atoms, substituted or unsubstituted, as defined above, or X is an alkylene chain of 1 carbon atom substituted with one or two, preferably one, substituent group(s) independently selected from alkyl and aryl, or X is a $CH_2$ group, with the proviso that where X is a $CH_2$ group then at least one of $R^1$, $R^2$ and $R^3$ are selected from alkyl and aryl, and prodrugs and pharmaceutically acceptable salts thereof.

The present invention also provides compounds per se of formulae (2), (3), (4) and (5):

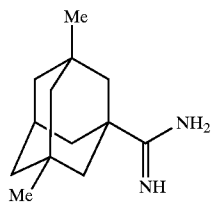

(2)

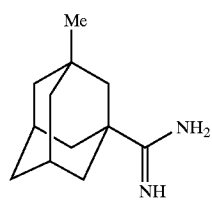

(3)

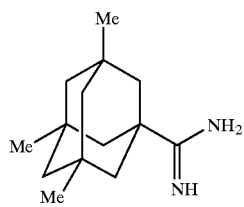

(4)

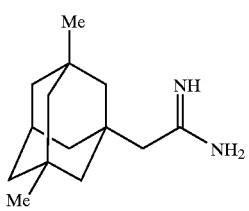

(5)

and prodrugs and pharmaceutically acceptable salts thereof.

The present invention also provides, for use in therapy:

(i) a compound of the formula (1) as defined above wherein at least one of $R^4$, $R^5$ and $R^6$ is alkyl, aryl, halogen or alkoxy, with the proviso that if $R^1$, $R^2$ and $R^3$ are hydrogen and $R^4$, $R^5$ and $R^6$ are independently selected from hydrogen and $C_{1-4}$ alkyl, then either X is an alkylene chain of 2–4 carbon atoms, substituted or unsubstituted, as defined above, or X is an alkylene chain of 1 carbon atom substituted with one or two, preferably one, substituent groups independently selected from alkyl and aryl;

(ii) a compound of the formula (1) as defined above wherein $R^4$, $R^5$ and $R^6$ are hydrogen and either X is an alkylene chain of 2–4 carbon atoms, substituted or unsubstituted, as defined above, or X is an alkylene chain of 1 carbon atom substituted with one or two, preferably one, substituent groups independently selected from alkyl and aryl, or X is a $CH_2$ group, with the proviso that where X is a $CH_2$ group then at least one of $R^1$, $R^2$ and $R^3$ are selected from alkyl and aryl; and (iii) a compound of formula (2), (3), (4) or (5) as defined above, and prodrugs and pharmaceutically acceptable salts thereof.

The present invention also provides a pharmaceutical composition comprising:

(i) a compound of the formula (1) as defined above wherein at least one of $R^4$, $R^5$ and $R^6$ is alkyl, aryl, halogen or alkoxy, with the proviso that if $R^1$, $R^2$ and $R^3$ are hydrogen and $R^4$, $R^5$ and $R^6$ are independently selected from hydrogen and $C_{1-4}$ alkyl then either X is an alkylene chain of 2–4 carbon atoms, substituted or unsubstituted, as defined above, or X is an alkylene chain of 1 carbon atom substituted with one or two, preferably one, substituent group independently selected from alkyl and aryl; or (ii) a compound of the formula (1) as defined above wherein $R^4$, $R^5$ and $R^6$ are hydrogen and either X is an alkylene chain of 2–4 carbon atoms, substituted or unsubstituted, as defined above, or X is an alkylene chain of 1 carbon atom substituted with one or two, preferably one, substituent groups independently selected from alkyl and aryl, or X is a $CH_2$ group, with the proviso that where X is a $CH_2$ group then at least one of $R^1$, $R^2$ and $R^3$ are selected from alkyl and aryl; or (iii) a compound of formula (2), (3), (4) or (5) as defined above, and prodrugs and pharmaceutically acceptable salts thereof, in combination with a pharmaceutically acceptable excipient.

According to a further aspect of the present invention there is provided a method of preparing the compounds of the present invention. Compounds of formula (1) may be prepared by conventional synthetic routes; see for example DD-A-151447, U.S. Pat. No. 5,061,703, DE-A-2306784, GB-1478477, Skwarski et al., Acta. Polon. Pharm., (1988), 45, 395–399 and May et al., Arzneim. Forsch., (1978), 28, 732–735, the disclosures of which are incorporated herein by reference.

The following reaction schemes describe examples of synthetic routes for the preparation of compounds falling within formula (1). The reaction schemes are included for the purpose of exemplification only and are not intended to be limiting to the invention.

Compounds of formula (1) may be synthesised by conventional synthetic methods as illustrated in Scheme 1.

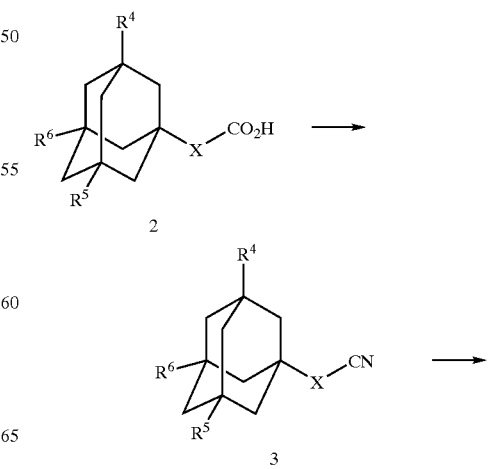

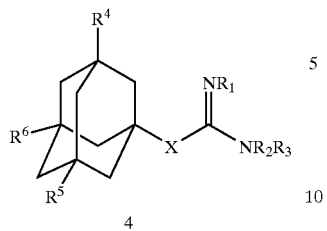

4

Amidines of formula 4 may be synthesised from nitrites of formula 3 by conventional methods, for example by treatment with an amine in the presence of trimethyl aluminium in a refluxing solvent such as toluene for several days, or alternatively by treatment with HCl in dry methanol at 0° C. for several days followed by treatment with $NH_3$ at room temperature. Nitriles of formula 3 may be synthesised from carboxylic acids of formula 2 by conventional methods, for example by treatment with methanesulphonyl chloride in the presence of pyridine, followed by treatment with $NH_3$, followed by treatment with methanesulphonyl chloride in the presence of pyridine. Carboxylic acids of formula 2 are either commercially available or may be synthesised by conventional methods such as those published in Stetter et al., Chem. Ber., 1962, 95, 667–672, by Koch et al., Chem. Ber., 1963, 96, 213–219, by Stepanov et al., Zh. Obstrich. Khim., 1964, 34, 579–584, by Stepanov et al., Zh. Org. Khim., 1965, 1, 280–283 and by Stepanov et al., Zh. Org. Khim., 1966, 2, 1612–1615.

An alternative route for the preparation of compounds of formula (1) where X is $CR^7R^8$ wherein $R^7$ and $R_1$ are independently hydrogen or alkyl and wherein $R^1$, $R^2$, $R^3$, $R^4$, $R^5$ and $R^6$ are as defined in formula (1), also involving conventional methods, is illustrated in Scheme 2.

Scheme 2

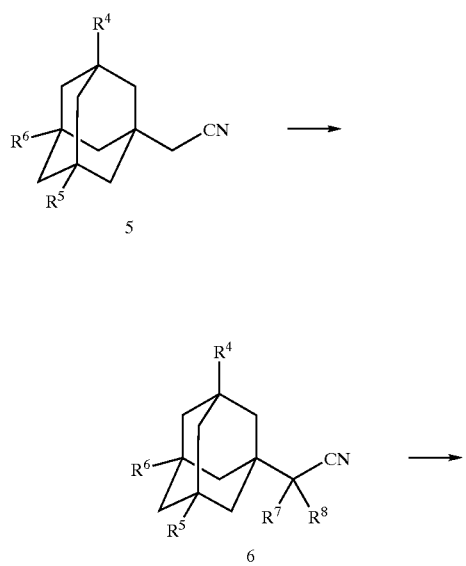

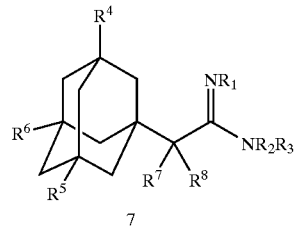

7

Amidines of formula 7 may be prepared from nitriles of formula 6 as described above. Nitriles of formula 6 may be prepared from nitriles of formula 5 by alkylation or dialkylation, for example by treatment with a base such as LDA followed by treatment with an alkyl halide. Further treatment with a base followed by a second alkyl halide would give the dialkylated nitrile.

An alternative route for the preparation of compounds of formula (1) where X is $CHR^9CH_2$ or $CH_2CHR^{10}$ wherein $R^9$ and $R^{10}$ are independently alkyl or aryl and wherein $R^1$, $R^2$, $R^3$, $R^4$, $R^5$ and $R^6$ are as defined above, also involving conventional methods, is illustrated in Scheme 3.

Scheme 3

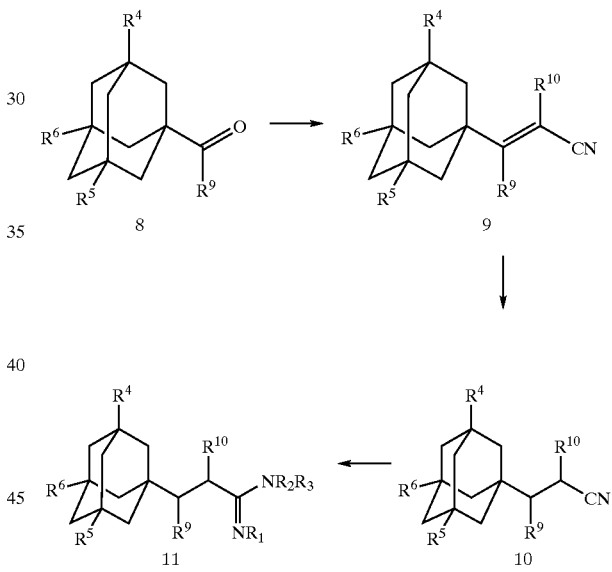

Amidines of formula 11 may be prepared from nitriles of formula 10 as described above. Nitriles of formula 10 may be prepared by reduction of unsaturated nitrites of formula 9, for example by hydrogenation in the presence of a transition metal catalyst such as palladium on carbon. Nitriles of formula 9 may be prepared from ketones or aldehydes of formula 8 by conventional methods such as the Homer-Emmons olefination reaction using an appropriately substituted phosphonate in the presence of a base such as sodium hydride. Ketones or aldehydes of formula 8 are commercially available or may be synthesised by conventional methods.

In addition, compounds of formula (1) where X is an alkylene chain of 3 or 4 carbon atoms may be synthesised by conventional methods as illustrated in Scheme 4. In Scheme 4, $R^1$, $R^2$, $R^3$, $R^4$, $R^5$ and $R^6$ are as defined above and $R^9$, $R^{10}$, $R^{11}$ and $R^{12}$ are independently selected from hydrogen, alkyl and aryl.

Scheme 4

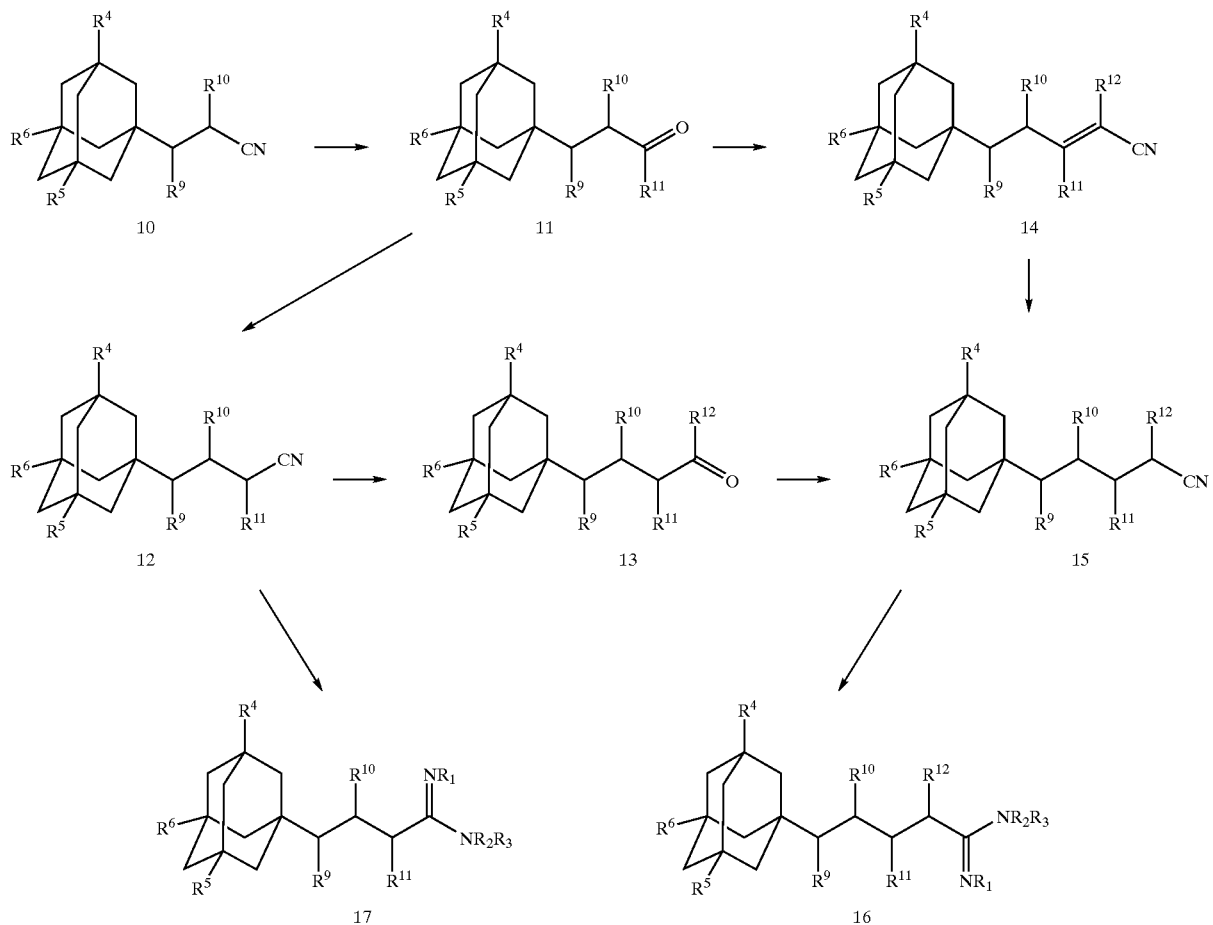

Anidines of formula 16 and 17 may be synthesised from nitrites of formula 15 and 12 respectively by the methods described in Scheme 1. Nitriles of formula 15 may be synthesised from nitriles of formula 14 by methods described in Scheme 3 or alternatively from ketones of formula 13 by reduction to the alcohol followed by tosylation or bromination, followed by cyanide displacement. Nitriles of formula 14 may be synthesised from ketones of formula 11 by methods described in Scheme 3. Ketones of formula 13 may be synthesised from nitrites of formula 12 by the addition of a Grignard reagent followed by hydrolytic work-up. Nitriles of formula 12 may be prepared from ketones of formula 11 by the reduction, tosylation/bromination and cyanide displacement sequence described above. Ketones of formula 11 may be prepared from nitrites of formula 10 by Grignard reactions as described above. Additional substituents may be introduced into the alkylene chain X by methods analagous to those described in the above schemes and by other conventional synthetic methods.

The compound of formula (1) may be administered in a form suitable for oral use, for example a tablet, pellet, capsule, aqueous or oily solution, suspension or emulsion; for topical use including transmucosal and transdermal use, for example a cream, ointment, gel, aqueous or oil solution or suspension, salve, patch or plaster; for nasal use, for example a snuff, nasal spray, nasal powder or nasal drops; for vaginal or rectal use, for example a suppository or pessary; for administration by inhalation, for example a finely divided powder or a liquid aerosol; for sub-lingual or buccal use, for example a tablet or capsule; for ocular use, for example a sterile aqueous solution or sterile ointment; or for parenteral use (including intravenous, subcutaneous, intramuscular, intravascular or infusion), for example a sterile aqueous or oil solution or suspension or emulsion, or depot injection formulation. In general the above compositions may be prepared in a conventional manner using conventional excipients, using standard techniques, including controlled release technologies, such as gelatin, lipid, gel depot, liposome and microcapsule based systems well known to those skilled in the art of pharmacy.

For oral administration, the compounds of the invention will generally be provided in the form of tablets or capsules or as an aqueous solution or suspension.

Tablets or pellets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, calcium hydrogen phosphate, cellulose derivatives and lactose, while corn starch and alginic acid are suitable disintegrating agents. Binding agents may include starch, gelatin and polyvinyl-pyrrolidone derivatives, while the lubricating agent, if present, will generally be magnesium stearate, stearic acid or talc. If desired, the tablets may be formulated or coated with a material such as glyceryl monostearate or glyceryl distearate or polymethacrylate polymers, cellulose derivatives or other pharmaceutically acceptable polymer, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions or emulsions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

Transdermal formulations include membrane permeation systems, multi-laminate adhesive dispersion systems and matrix dispersion systems. Transdermal delivery also includes the use of electrically aided transport and skin penetration enhancers and needle-free injection devices.

The preferred route of administration will be as an intravenous infusion, preferably over a period of up to seven days, or as an oral formulation, or as an intramuscular injection via a styrette or as a subcutaneous injection.

It will be appreciated that the dosage levels used may vary over quite a wide range depending upon the compound used, the severity of the condition exhibited by the patient and the patient's body weight. However, without commitment to a rigid definition of dosages it may be stated that a daily dosage of the active constituent (estimated as the free base) is 100 $\mu$g to 800 mg. More particularly, the preferred compounds may be administered at a preferred dose of 50–800 mg/day, in single or divided doses.

The invention will now be described in detail. It will be appreciated that the invention is described by way of example only and modification of detail may be made without departing from the scope of the invention.

EXPERIMENTAL

I Synthesis

Example 1

3,5-Dimethyl-1-adamantanecarboximidamide hydrochloride 3,5-Dimethyl-1-adamantanecarbonitrile A solution of 3,5-dimethyl-1-adamantanecarboxylic acid (2.51 g, 12.1 mmol) in dry pyridine (40 mL) at 0° C. was treated dropwise with methanesulphonyl chloride (1.4 g, 12.2 nmmol), stirred for 2 h, saturated with ammonia gas, stirred for 5 min and the excess ammonia removed in vacuo. The resulting suspension at 0° C. was treated with methanesulphonyl chloride (11.8 g, 102 mmol), stirred overnight at room temperature, poured into cold 1-M HCl (200 mL) and extracted with EtOAc (3×40 mL). The organic phase was washed with dilute HCl (50 mL), water (50 mL), dried (MgSO$_4$), concentrated in vacuo and the residue purified by chromatography [SiO$_2$; CH$_2$Cl$_2$] to give the product (1.97 g, 86%) as a pale brown oil: IR $v_{max}$ (liquid film)/cm$^{-1}$ 2922, 2849, 2235, 1455, 1359 and 1098; NMR $\delta_H$ (400 MHz, CDCl$_3$) 0.87 (6H, s), 1.19 (2H, s), 1.3–1.45 (4H, m), 1.55–1.75 (4H, m), 1.8–1.9 (2H, m) and 2.1–2.15 (1H, m).

3,5-Dimethyl-1-adamantanecarboximidamide hydrochloride

A solution of 3,5-dimethyl-1-adamantanecarbonitrile (1.95 g, 10.3 mmol) in MeOH (30 mL) at 0° C. was saturated with HCl gas over 30 min, left at 0° C. for 5 days, concentrated in vacuo, the residue triturated with EtOAc and filtered to give the intermediate imidate hydrochloride salt (1.16 g, 44%) as a hygroscopic solid. The solid (302 mg, 1.17 mmol) in MeOH (20 mL) at 0° C. was saturated with ammonia gas, left at room temperature for 4 days, concentrated to a small volume in vacuo, treated with EtOAc and filtered to give the title compound (240 mg, 85%) as a white crystalline solid: mp 297–229° C.; IR $v_{max}$ (Nujol)/cm$^{-1}$ 3166, 1673, 1508, 1087 and 729; NMR $\delta_H$ (400 MHz, DMSO-d$_6$) 0.85 (6H, s), 1.20–1.50 (2H, m), 1.30–1.40 (4H, m), 1.40–1.60 (4H, m), 1.69 (2H, m), 2.12 (2H, m), 8.55 (2H, br s) and 8.90 (2H, br s); Anal. Calcd for C$_{13}$H$_{23}$N$_2$Cl.0.1 H$_2$O: C, 68.84; H, 9.56; N, 11.45. Found: C, 63.73; H, 9.34; N, 11.46.

Example 2

3-Chloro-1-adamantanecarboximidamide hydrochloride

3-Chloro-1-adamantanecarbonitrile

This was prepared from 3-chloro-1-adamantanecarboxylic acid by the method of example 1 and the product isolated (2.12 g, 94%) as a pale brown solid: mp 156–157° C.; IR $v_{max}$ (Nujol)/cm$^{-1}$ 2249, 2230, 1248, 1124, 972 and 734; NMR $\delta_H$ (400 MHz, CDCl$_3$) 1.64–1.73 (2H, m), 1.96–2.04 (4H, m), 2.07–2.16 (4H, m), 2.25–2.30 (2H, m) and 2.38 (2H, s); Anal. Calcd for C$_{11}$H$_{14}$NCl: C, 67.52; H, 7.21; N, 7.15. Found: C, 67.52; H, 7.18; N, 6.94.

3-Chloro-1-adamantanecarboximidamide hydrochloride

This was prepared from 3-chloro-1-adamantanecarbonitrile by the method of example 1 and the title compound isolated (272 mg, 96%) as a white crystalline solid: mp 215–216° C.; IR $v_{max}$ (Nujol)/cm$^{-1}$ 3455, 3376, 3306, 3148, 1687, 1667, 1082, 837, 733 and 701; NMR $\delta_H$ (400 MHz, DMSO-d$_6$) 1.55–1.65 (2H, m), 1.80–1.90 (4H, m), 2.05–2.15 (4H, m), 2.25 (2H, s), 2.28 (2H, s), 8.70 (2H, s) and 9.04 (2H, s); Anal. Calcd for C$_{11}$H$_{18}$N$_2$Cl$_2$.H$_2$O.0.1 NH$_4$Cl: C, 48.48; H, 7.54; N, 10.79. Found: C, 48.81; H, 7.63; N, 10.86.

Example 3

3-Bromo-1-adamantanecarboximidamide hydrochloride

This was prepared from 3-bromo-1-adamantanecarbonitrile by the method of example 1 and the title compound isolated (276 mg, 97%) as a white crystalline solid: mp 221–223° C.; IR $v_{max}$ (Nujol)/cm$^{-1}$ 3453, 3373, 3307, 3152, 1687, 1667, 1081, 825, 722, 699 and 679; NMR $\delta_H$ (400 MHz, DMSO-d$_6$) 1.60–1.70 (2H, m), 1.85–1.95 (4H, m), 2.21 (2H, s), 2.25–2.35 (4H, m), 2.50 (2H, s) and 8.8 (4H, br s); Anal. Calcd for C$_{11}$H$_{18}$N$_2$BrCl.H$_2$O: C, 42.39; H, 6.47; N, 8.99. Found: C, 42.17; H, 6.48; N, 9.08.

Example 4

3-Ethyl-1-adamantanecarboximidamide hydrochloride

This was prepared from 3-ethyl-1-adamantanecarbonitrile by the method of example 1 and the title compound isolated (1.74 g, 94%) as a white crystalline solid: mp 210–212° C.; IR $v_{max}$ (Nujol)/cm$^{-1}$ 3266, 3070, 1665, 1089 and 734;

NMR δ$_H$ (400 MHz, DMSO-d$_6$) 0.79 (3H, t, J7.75 Hz), 1.1–1.2 (2H, m), 1.35–1.45 (4H, m), 1.7–1.85 (2H, m), 2.09 (2H, s), 8.56 (2H, br s) and 8.92 (2H, br s); Anal. Calcd for C$_{13}$H$_{23}$N$_2$Cl: C, 64.31; H, 9.55; N, 11.53.Found: C, 64.05; H, 9.95; N, 11.49.

Example 5

3,5-Dimethyl-1-adamantaneacetiniidamide hydrochloride 3,5-Dimethyl-1-adamantaneacetonitrile This was prepared from 3,5-dimethyl-1-adamantaneacetic acid (Bott and Hellman, Angew. Chem. Int. Ed. Engl., 1966, 5,870, the disclosure of which is incorporated herein by reference) by the method of example 1 and the product isolated (833 mg, 88%) as a pale brown oil: IR ν$_{max}$ (liquid film)/cm$^{-1}$ 2900, 2843, 2244, 1455, 1360 and 1345; NMR δ$_H$ (400 MHz, CDCl$_3$) 0.84 (6H, s), 1.1–1.3 (6H, m), 1.32–1.35 (2H, m), 1.44–1.47 (2H, m), 2.12 (2H, s) and 2.05–2.15 (1H, m).

3,5-Dimethyl-1-adamantaneacetimidamide hydrochloride

This was prepared from 3,5-dimethyl-1-adamantaneacetonitrile by the method of example 1 and the title compound isolated (778 mg, 100%) as a white crystalline solid: mp 252–253° C.; IR ν$_{max}$ (Nujol)/cm$^{-1}$ 3384, 3076, 1691 and 722; NMR δ$_H$ (400 MHz, DMSO-d$_6$) 0.81 (6H, s), 1.0–1.25 (6H, m), 1.25–1.35 (4H, m), 1.38 (2H, s), 2.04 (1H, m), 2.17 (2H, s) and 8.76 (4H, br s); Anal. Calcd for C$_{14}$H$_{25}$N$_2$Cl.0.9 H$_2$O: C, 61.59; H, 9.89; N, 10.26. Found: C, 61.69; H, 10.31; N, 10.19.

Example 6

N-Allyl-3,5-dimethyl-1-adamantanecarboximidamide hydrochloride

This was prepared from 3,5-dimethyl-1-adamantanecarbonitrile by the method of example 1 using allylamine (3 eq) instead of ammonia. The title compound was isolated (46 mg, 42%) as a white crystalline solid: mp 222–224° C.; IR ν$_{max}$ (Nujol)/cm$^{-1}$ 3039, 1671, 1614, 993, 932, 810 and 722; NMR δ$_H$ (400 MHz, DMSO-d$_6$) 0.85 (6H, s), 1.16–1.19 (2H, m), 1.3–1.4 (4H, m), 1.48–1.6 (4H, m), 1.75 (2H, m), 2.14 (1H, m), 3.92 (2H, m), 5.10–5.20 (2H, m), 5.75–5.85 (1H, m), 8.7 (2H, br s) and 9.0 (1H, br s); Anal. Calcd for C$_{16}$H$_{27}$N$_2$Cl.0.2 H$_2$O: C, 67.09; H, 9.64; N, 9.78. Found: C, 67.09; H, 9.56; N, 9.53.

Example 7

N-Allyl-1-adamantanecarboximidamide hydrochloride

This was prepared from 1-adamantanecarbonitrile by the method of example 1 using allylamine (3 eq) instead of ammonia. The title compound was isolated (298 mg, 90%) as a white crystalline solid: mp 252–254° C.; IR ν$_{max}$ (Nujol)/cm$^{-1}$ 3185, 3031, 1678, 1613, 1257, 799, 751 and 717; NMR δ$_H$ (400 MHz, DMSO-d$_6$) 1.65–1.70 (6H, m), 1.9–2.0 (6H, m), 2.04 (3H, s), 3.95 (2H, m), 5.1–5.2 (2H, m), 5.75–5.85 (1H, m), 8.71 (1H, s), 8.79 (1H, s) and 9.15 (1H, s); Anal. Calcd for C$_{14}$H$_{23}$N$_2$Cl: C, 65.99; H, 9.10; N, 10.99. Found: C, 65.92; H, 9.04; N, 11.05.

Example 8

N-Ethyl-1-adamantanecarboximidainide hydrochloride

This was prepared from 1-adamantanecarbonitrile by the method of example 1 using 2-M ethylamine in MeOH (3 eq) in place of ammonia and the title compound isolated (175 mg, 55%) as a white crystalline solid: mp 315° C. (dec); IR ν$_{max}$ (Nujol)/cm$^{-1}$ 3191, 3030, 1682, 1616, 1354, 810 and 766; NMR δ$_H$ (400 MHz, DMSO-d$_6$) 1.10 (3H, t, J 7.0 Hz), 1.6–1.7 (6H, m), 1.85–1.90 (6H, m), 2.0–2.05 (3H, m), 3.30 (2H, pent, J 7.0 Hz), 8.67 (1H, s), 8.71 (1H, s) and 8.86 (1H, s); Anal. Calcd for C$_{13}$H$_{23}$N$_2$Cl: C, 64.31; H, 9.55; N, 11.54. Found: C, 64.27; H, 9.56; N, 11.54.

Example 9

N-Benzyl-1-adamantanecarboximidamide hydrochloride

This was prepared from 1-adamantanecarbonitrile by the method of example 1 using benzylamine (1.1 eq) in place of ammonia and the title compound isolated (357 mg, 90%) as a white crystalline solid: mp 242–244° C.; IR ν$_{max}$ (Nujol)/cm$^{-1}$ 3049, 1677, 1605, 1240, 759, 728 and 703; NMR δ$_H$ (400 MHz, DMSO-d$_6$) 1.65–1.70 (6H, m), 1.9–2.0 (6H, m), 2.05 (3H, s), 4.58 (2H, s), 7.3–7.4 (5H, m), 8.80 (1H, s), 8.85 (1H, s) and 9.55 (1H, s); Anal. Calcd for C$_{18}$H$_{25}$N$_2$Cl: C,70.92; H, 8.27; N, 9.18. Found: C, 70.62; H, 8.21; N, 9.18.

Example 10

N-(2-Dimethylaminoethyl)-1-adamantanecarboximidamide dihydrochloride

This was prepared from 1-adamantanecarbonitrile by the method of example 1 using N,N-dimethylethylenediamine (3 eq) in place of ammonia and the title compound isolated (42 mg, 10%) as a white crystalline solid: mp 293° C. (dec); IR ν$_{max}$ (Nujol)/cm$^{-1}$ 3192, 2581, 2469, 1697, 1605 and 798; NMR δ$_H$ (400 MHz, DMSO-d$_6$) 1.65–1.75 (6H, m), 1.94 (6H, s), 2.04 (3H, s), 2.81 (6H, s), 3.27 (2H, m), 3.72 (2H, m), 8.98 (1H, s), 9.04 (1H, s), 9.13 (1H, s) and 10 86 (1H, s); Anal. Calcd for C$_{15}$H$_{29}$N$_3$Cl$_2$.0.25 H$_2$O: C, 55.12; H, 9.10; N, 12.86. Found: C, 55.23; H, 9.00; N, 12.89.

Example 11

3-(3,5-Dimethyl-1-adamantyl)propanimidamide hydrochloride 3-(3,5-Dimethyl-1-adamantyl)propionitrile A solution of 1-bromo-3,5-dimethyladamantane (1.0 g, 4.11 mmol), acrylonitrile (436 mg, 8.22 mmol) and 1,1'-azobis(cyclohexanecarbonitrile) (50 mg, 0.21 mmol) in dry toluene (12 mL) was treated with tri-n-butyltin hydride (1.44 g, 4.93 mmol) at room temperature, refluxed for 3.5 h, cooled, diluted with ether (30 mL), washed with 0.2-M NH$_4$OH (30 mL), water (10 mL), dried (MgSO$_4$) and concentrated in vacuo. The residue was purified by chromatography [SiO$_2$, CH$_2$Cl$_2$-hexane (0:100 to 100:0)] to give the product (771 mg, 86%) as a colourless oil: IR ν$_{max}$ (liquid film)/cm$^{-1}$ 2899, 2841, 2247, 1545 and 1359; NMR δ$_H$ (400 MHz, CDCl$_3$) 0.81 (6H, s), 1.0–1.2 (6H, m), 1.25–1.35 (6H, m), 1.53 (2H, t, J 4.2 Hz), 2.05–2.10 (1H, m) and 2.27 (2H, tJ 4.2 Hz).

3-(3,5-Dimethyl-1-adamantyl)propanimidamide hydrochloride

This was prepared from 3-(3,5-dimethyl-1-adamantyl) propionitrile by the method of example 1 and the title compound isolated (609 mg, 86%) as a white crystalline solid: mp 246–248° C.; IR ν$_{max}$ (Nujol)/cm$^{-1}$ 3076, 1681, 789 and 749; NMR δ$_H$ (400 MHz, DMSO-d$_6$) 0.80 (6H, s), 1.08 (6H, q, J 12.5 Hz), 1.28 (6H, d J 2.6 Hz), 1.39 (2H, m), 2.02 (1H, m), 2.31 (2H, m), 8.65 (2H, br s) and 8.99 (2H, br s); Anal. Calcd for C$_{15}$H$_{25}$N$_2$Cl.0.2 NH$_4$Cl: C, 63.99; H, 9.95; N, 10.95. Found: C, 64.15; H, 9.98; N, 10.87.

Example 12

3-Methyl-1-adamantanecarboximidamide hydrochloride

3-Methyl-1-adamantanecarbonitrile

This was prepared from 3-methyl-1-adamantanecarboxylic acid by the method of example 1 and the product (1.81 g, 80%) isolated as a pale brown waxy solid: IR $v_{max}$ (Nujol)/cm$^{-1}$ 2923, 2853, 2233, 1456, 1377, 1360, 1343, 1161 and 1111; NMR $\delta_H$ (400 MHz, CDCl$_3$) 0.85 (3H, s), 1.45 (4H, m), 1.63 (2H, m), 1.74 (2H, s), 1.94 (4H, m) and 2.07 (2H, m).

3-Methyl-1-adamantanecarboximidamide hydrochloride

This was prepared from 3-methyl-1-adamantanecarbonitrile by the method of example 1 and the title compound (1.26 g, 95%) isolated as a white crystalline solid: mp 255–257° C.; IR $v_{max}$ (Nujol)/cm$^{-1}$ 3222, 3084, 2923, 2853, 1674, 1502, 1456, 1376, 1087 and 737; NMR $\delta_H$ (400 MHz, DMSO-d$_6$) 0.83 (3H, s), 1.42 (4H, m), 1.58 (4H, m), 1.77 (4H, m), 2.07 (2H, m), 8.61 (2H, br s) and 8.99 (2H, br s); NMR $\delta_C$ (100 MHz, DMSO-d$_6$) 28.1, 30.2, 30.8, 34.9, 37.5, 42.7, 44.6 and 177.0.

Example 13

3,5,7-Trimethyl-1-adamantanecarboximidamide hydrochloride

3,5,7-Trimethyl-1-adamantanecarbonitrile

This was prepared from 3,5,7-trimethyl-1-adamantanecarboxylic acid by the method of example 1 and the product (2.01 g, 88%) isolated as a waxy solid: IR $v_{max}$ (Nujol)/cm$^{-1}$ 2923, 2864, 2230, 1456, 1377, 1358, 1350, 1257, 1095 and 912; NMR $\delta_H$ (400 MHz, CDCl$_3$) 0.90 (9H, s), 1.12 (6H, m) and 1.60 (6H, s).

3,5,7-Trimethyl-1-adamantanecarboximidamide hydrochloride

This was prepared from 3,5,7-trimethyl-1-adamantanecarbonitrile by the method of example 1 and the title compound (0.98 g, 98%) isolated as a white crystalline solid: mp 325° C.; IR $v_{max}$ (Nujol)/cm$^{-1}$ 3266, 3094, 2923, 2854, 1666, 1517, 1454, 1376, 1365, 1113, 1098 and 741; NMR $\delta_H$ (400 MHz, DMSO-d$_6$) 0.86 (9H, s), 1.09 (6H, m), 1.44 (6H, s), 8.59 (2H, br s) and 8.99 (2H, br s); NMR $\delta_C$ (100 MHz, DMSO-d$_6$) 30.0, 31.8, 40.9, 43.5, 49.2 and 176.7.

Example 14

3-(4-Nitrophenyl)-1-adamantanecarboximidamide hydrochloride

3-(4-Nitrophenyl)-1-adamantanecarbonitrile

This was prepared from 3-(4-nitrophenyl)-1-adamantanecarboxylic acid by the method of example 1 and the product (0.92 g, 93%) isolated as a pale brown solid: IR $v_{max}$ (Nujol)/cm$^{-1}$ 2923, 2854, 2235, 1594, 1516, 1458, 1377, 1353, 1111 and 858; NMR $\delta_H$ (400 MHz, CDCl$_3$) 1.79 (2H, m), 1.94 (4H, m), 2.11 (4H, m), 2.21 (2H, s), 2.30 (2H, m), 7.49 (2H, m) and 8.20 (2H, m).

3-(4-Nitrophenyl)-1-adamantanecarboximidamide hydrochloride

This was prepared from 3-(4-nitrophenyl)-1-adamantanecarbonitrile by the method of example 1 and the title compound (0.22 g, 77%) isolated as a white crystalline solid: mp 256–259° C.; IR $v_{max}$ (Nujol)/cm$^{-1}$ 3448, 3365, 3314, 3160, 3074, 2923, 2854, 1686, 1664, 1608, 1596, 1512, 1455, 1377, 1351, 741 and 697; NMR $\delta_H$ (400 MHz, DMSO-d$_6$) 1.72 (2H, m), 1.93 (8H, m), 2.09 (2H, s), 2.25 (2H, m), 7.75 (2H, m), 8.21 (2H, m), 8.73 (2H, br s) and 8.93 (2H, br s).

Example 15

2-(1-Adamantyl)butanimidamide hydrochloride

2-(1-Adamantyl)butanenitrile

A solution of diisopropylamine (0.45 mL, 3.2 mmol) in dry THF (15 mL) at −78° C. was treated with n-BuLi (1.6-M, 2 mL, 3.2 mmol), stirred at −78° C. for 15 min, treated with a solution of 2-(1-adamantyl)acetonitrile (0.5 g, 2.9 mmol) in dry THF (5 mL) and stirred at −78° C. for 1 h. Ethyl iodide (0.26 mL, 3.2 mmol) was added dropwise, the solution stirred at −78° C. for 2 h, allowed to warm to room temperature, treated with NH$_4$Cl solution (20 mL), extracted with EtOAc (3×10 mL), the extracts washed with brine (10 mL), dried (MgSO$_4$) and concentrated in vacuo to give the product (0.56 g, 97%) as a pale brown solid: mp 53–54° C; IR $v_{max}$ (Nujol)/cm$^{-1}$ 2914, 2231, 1455, 1378, 1366, 1346, 1317, 1091 and 979;.NMR $\delta_H$ (400 MHz, CDCl$_3$) 1.11 (3H, t, J 7.4 Hz), 1.49 (1H, m), 1.74–1.64 (13H, m) and 2.06 (4H, m); Anal. Calcd for C$_{14}$H$_{21}$N.0.1 H$_2$O: C, 81.97; H, 10.42; N, 6.83. Found: C, 81.92; H, 10.68; N, 6.74.

2-(1-Adamantyl)butanimidamide hydrochloride

A suspension of NH$_4$Cl (1.38 g, 26 mmol) in dry toluene (8 mL) at 0° C. was treated dropwise with 2-M trimethylaluminium in toluene (13 mL, 26 mmol), allowed to warm to room temperature and stirred for 2 h. This solution was added to a solution of 2-(1-adamantyl)butanenitrile (0.44 g, 2.2 mmol) in dry toluene (10 mL) and the resulting solution refluxed for 4 days, cooled to room temperature and poured into a slurry of SiO$_2$ (5 g) and CHCl$_3$ (10 mL). The slurry was filtered, the filtrate treated with Na$_2$SO$_4$, concentrated in vacuo and the residue loaded on to the top of a silica column and purified by chromatography [SiO$_2$; EtOAc-MeOH (9:1 to 4:1)] to give the title compound (0.38 g, 68%) as a white solid: mp 223° C. (dec); IR $v_{max}$ (Nujol)/cm$^{-1}$ 3332, 3157, 3071, 2925, 2852, 1666, 1510, 1462, 1377 and 724; NMR $\delta_H$ (400 MHz, DMSO-d$_6$) 0.81 (3H, t, J 7.2 Hz), 1.39 (2H, m), 1.56–1.69 (11H, br m), 1.96 (3H, m), 2.13 (1H, m) and 9.08 (4H, br m); NMR $\delta_C$ (100 MHz, DMSO-d$_6$) 11.8, 17.0, 27.8, 34.1, 36.2, 39.5, 56.0 and 171.0.

Example 16

2-(1-Adamantyl)-3-phenylpropanimidamide hydrochloride

This was prepared from 2-(1-adamantyl)-2-phenylpropanenitrile by the method of example 15 and the title compound (0.11 g, 46%) isolated as a white crystalline solid: mp 147–148° C.; IR $v_{max}$ (Nujol)/cm$^{-1}$ 3250 br, 2923, 2852, 1679, 1495, 1456, 1377, 1346, 1313, 1084, 739 and 699; NMR $\delta_H$ (400 MHz, DMSO-d$_6$) 1.51 (3H, m), 1.66 (6H, m), 1.79 (3H, m), 2.01 (3H, m), 2.60 (1H, m), 2.96 (2H, m), 7.24 (5H, m), 8.60 (1H, br s), 8.78 (1H, br s), 8.92 (1H, br s) and 9.05 (1H, br s).

Example 17

3-(1-Adamantyl)-2-phenylpropanimidamide hydrochloride

3-(1-Adamantyl)-2-phenylpropenenitrile

A solution of diethyl 1-cyano-1-phenylmethylphosphonate (10.97 g, 43.3 mmol) in dry THF (60 mL) at 0° C. was treated with NaH (60% dispersion in oil, 1.7 g, 43.3 mmol), stirred at 0° C. for 40 min, warmed to room temperature for 20 min, treated with a solution of 1-adamantanecarboxaldehyde (3.56 g, 21.7 mmol) in dry THF (10 mL) and heated at 60° C. for 16 h. The reaction mixture was cooled, treated with water (50 mL), extracted with EtOAc (3×20 mL), the extracts washed with brine (40 mL), dried (MgSO$_4$) and concentrated in vacuo. The resulting brown oil was purified by chromatography [SiO$_2$, heptane-EtOAc (9:1)] and recrystallised (heptane) to give the product (1.62 g, 28%) as a white solid: mp 107–108° C; IR $v_{max}$ (Nujol)/cm$^{-1}$ 2924, 2852, 2218, 1497, 1448, 1377, 1343, 1101, 910, 762, 750 and 689; NMR $\delta_H$ (400 MHz, CDCl$_3$) 1.76 (6H, m), 1.99 (6H, m), 2.07 (3H, m), 6.50 (1H, s), 7.37 (3H, m) and 7.51 (2H, m); Anal. Calcd for C$_{19}$H$_{21}$N: C, 86.65; H, 8.04; N, 5.32. Found: C, 86.58; H, 8.09; N, 5.33.

3-(1-Adamantyl)-2-phenylpropanenitrile

A solution of 3-(1-adamantyl)-2-phenylpropenenitrile (600 mg, 2.28 mmol) in EtOAc (30 mL) was treated with 10% Pd/C (70 mg), hydrogenated at 50 psi for 16 h, filtered through SiO$_2$ and concentrated in vacuo. The residue was purified by chromatography [SiO$_2$, EtOAc-heptane (1:1)] and the resulting solid recrystallised (heptane) to give the product (552 mg, 91%) as a white crystalline solid: mp 83–84° C; IR $v_{max}$ (Nujol)/cm$^{-1}$ 2912, 2852, 2239, 1497, 1453, 1377, 1355, 1346, 1105, 749, 713 and 696; NMR $\delta_H$ (400 MHz, CDCl$_3$) 1.50 (1H, dd, J 14.3, 3.2 Hz), 1.63 (9H, m), 1.72 (3H, m), 1.94 (1H, dd, J 14.3,10.4 Hz), 2.01 (3H, m), 3.79 (1H, dd, J 10.4, 3.2 Hz) and 7.35 (5H, m); Anal. Calcd for C$_{19}$H$_{23}$N: C, 85.99; H, 8.73; N, 5.28. Found: C, 85.96; H, 8.90; N, 5.27.

3-(1-Adamantyl)-2-phenylpropanimidamide hydrochloride

This was prepared from 3-(1-adamantyl)-2-phenylpropanenitrile by the method of example 15 and the title compound (92 mg, 60%) isolated as a pale brown solid: mp 253° C. (dec); IR $v_{max}$ (Nujol)/cm$^{-1}$ 3243, 2918, 2853, 1680, 1496, 1455, 1377, 1105, 1080, 754, 721 and 705; NMR $\delta_H$ (400 MHz, DMSO-d$_6$) 1.40 (3H, m), 1.55 (7H, m), 1.68 (3H, m), 1.92 (3H, m), 2.15 (1H, m), 4.05 (1H, m), 7.31 (1H, m), 7.40 (2H, m), 7.52 (2H, m) and 9.01 (4H, br s).

Example 18

3-(1-Adamantyl)-3-phenylpropanimidamide hydrochloride

This was prepared from 3-(1-adamantyl)-3-phenylpropanenitrile by the method of example 15 and the title compound (130 mg, 50%) isolated as a pale yellow solid: mp 249° C. (dec); IR $v_{max}$ (Nujol)/cm$^{-1}$ 3400–2800 br, 2957, 1684, 1455, 1407, 1377, 772 and 704; NMR $\delta_H$ (400 MHz, DMSO-d$_6$) 1.37 (3H, m), 1.51 (6H, m), 1.60 (3H, m), 1.92 (3H, m), 2.91 (3H, m), 7.25 (5H, m), 8.50 (2H, br s) and 9.00 (2H, br s).

II NMDA Receptor Binding

The NMDA receptor contains several distinct binding domains that can regulate opening of the cationic channel. The phencyclidine (PCP) site of the NMDA receptor can be radiolabeled with [$^3$H]-(+)-5-methyl-10,11-dihydro-5H-dibenzo[a,d]cyclohepten-5,10-imine hydrogen maleate, [$^3$H-MK-801]. The following describes the procedure for determining the affinity of compounds for the PCP site in rat cortical or cerebellar membranes.

Frozen rat cortex or cerebellum, homogenized in 10 volumes of ice cold 0.32 M. sucrose is centrifuged at 1,000 g for 12 min and the supernatant stored on ice whilst the pellet was resuspended, rehomogenized and recentrifuged twice more. The three final supernatants were pooled and centrifuged at 30,000 g for 40 min at 4° C. to yield P$_2$ pellets. These were resuspended in ice-cold distilled water, and centrifuged at 30,000 g for 50 min at 4° C. Following three further washes in distilled water, the P$_2$ pellets were stored at −20° C. for at least 18 h. On the day of the assay, membrane pellets were thawed at room temperature, resuspended in ice-cold distilled water and centrifuged at 30,000 g for 20 min. The pellets were resuspended in 50 mM tris-HCl (pH:7.4) and recentrifuged twice more before being resuspended in tris-HCl for immediate use in the assay. Binding assays were performed at equilibrium in a total volume of 200 μl, containing, [$^3$H]-MK-801 (5 nM final conc.), 10 μM glutamate, 10 μM glycine, 160 μl of membrane preparation and additional drugs where appropriate. Non-specific binding was determined using MK-801 (10 μM). The assay was incubated for 120 min at room temperature. The incubation was terminated by rapid filtration through Whatman GF/B filters (pre-soaked in 0.1% PEI solution). The assay tubes and filters were washed five times with 1 ml of ice cold assay buffer. The filters were placed in poly-Q mini vials with approximately 5 ml of scintillation fluid. The vials are then shaken and left for at least 8 hours before being counted on a liquid scintillation counter. To determine the free ligand concentration 3 aliquots (20 μl) of the [$^3$H]-MK-801 working solution were also counted. Concentration response data for drugs was analysed using a 4 parameter equation fitted by non linear regression. This yielded the half maximally effective drug concentration (IC$_{50}$) and Hill coefficient.

The data obtained from these assays are presented in Table 1. The data clearly demonstrate that the compounds of the invention are active as NMDA antagonists and have favourable ratios of cortical to cerebellar binding affinity indicating that the compounds will be well-tolerated in vivo.

TABLE 1

Binding Affinities at Cortical and Cerebellar NMDA Receptors

| Compound | IC$_{50}$(μM) Cortex | IC$_{50}$(μM) Cerebellum | Ratio |
|---|---|---|---|
| Example 1 | 28 | 6 | 4.7 |
| Example 2 | 291 | | |
| Example 3 | 188 | 105 | 1.8 |
| Example 4 | 122 | 56 | 2.2 |
| Example 5 | 82 | 56 | 1.5 |
| Example 6 | 31 | | |
| Example 7 | 698 | 297 | 2.4 |
| Example 8 | 1000 | | |
| Example 9 | 754 | 388 | 1.9 |
| Example 10 | 1000 | | |
| Example 11 | 78 | 48 | 1.6 |
| Example 12 | 96 | 36 | 2.7 |
| Example 13 | 43 | 18 | 2.4 |
| Example 14 | 406 | 234 | 1.7 |
| Example 15 | 144 | 46 | 3.1 |
| Example 16 | 52 | 27 | 1.9 |
| Example 17 | 16 | | |
| Example 18 | 27 | | |

What is claimed is:

1. A method of treating a condition treatable by antagonism of the N-methyl-D-aspartate receptor, which comprises administering to a patient in need of said treatment of said condition, a pharmaceutically effective dose of a compound of the formula (1):

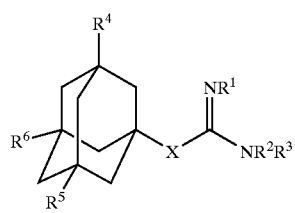

wherein
- X is an alkylene chain containing 0, 1, 2, 3 or 4 carbon atoms;
- $R^1$, $R^2$ and $R^3$ are independently selected from hydrogen, alkyl and aryl;
- $R^4$, $R^5$ and $R^6$ are independently selected from hydrogen, alkyl, aryl, halogen and alkoxy;

or a prodrug or pharmaceutically acceptable salt thereof.

2. The method of claim 1 wherein X is an alkylene chain containing 1, 2, 3 or 4 carbon atoms and one or more carbon atom(s) of the chain X is/are independently substituted by substituent group(s) selected from alkyl and aryl.

3. The method of claim 2 wherein a substituted carbon atom is substituted by one substituent group selected from alkyl and aryl.

4. The method of claim 2 wherein a substituted carbon atom is substituted by two substituent groups independently selected from alkyl and aryl.

5. The method of claim 2, wherein the substituent group(s) are selected from methyl, ethyl, phenyl and benzyl.

6. The method of claim 2, wherein one carbon atom of the chain X is substituted.

7. The method of claim 1 wherein X is $(CH_2)_n$ where n=0 to 4.

8. The method of claim 1 wherein X is an alkylene chain containing 1 or 2 carbon atoms in the chain.

9. The method of claim 7 wherein n=0.

10. The method of claim 1 wherein $R^1$ and $R^2$ are hydrogen and $R^3$ is selected from hydrogen, alkyl and aryl.

11. The method of claim 1 wherein $R^1$, $R^2$ and $R^3$ are hydrogen.

12. The method of claim 1 wherein at least one of $R^4$, $R^5$ and $R^6$ is alkyl, aryl, halogen or alkoxy.

13. The method of claim 1 to wherein $R^4$ is selected from hydrogen, alkyl and halogen.

14. The method of claim 1 wherein $R^5$ is selected from hydrogen and alkyl.

15. The method of claim 1 wherein $R^6$ is selected from hydrogen and alkyl.

16. The method of claim 1 wherein X has 0 carbon atoms; $R^1$, $R^2$ and $R^3$ are hydrogen; $R^4$ and $R^5$ are $CH_3$; and $R^6$ is hydrogen.

17. The method of claim 1 wherein X has 0 carbon atoms; $R^1$, $R^2$ and $R^3$ are hydrogen; $R^4$ is methyl; and $R^5=R^6=$ hydrogen or methyl.

18. The method of claim 2 wherein X has one carbon atom and is substituted by an ethyl or benzyl group; and $R^1$, $R^2$, $R^3$, $R^4$, $R^5$ and $R^6$ are hydrogen.

19. The method of claim 1 wherein X has one carbon atom and is unsubstituted; $R^1$, $R^2$ and $R^3$ are hydrogen; $R^4$ and $R^5$ are methyl and $R^6$ is hydrogen.

20. The method of claim 1 wherein said condition treatable by blockade of the N-methyl-D-aspartate receptor is selected from the group consisting of ischaemic stroke, haemorrhagic stroke, Alzheimer's disease, multiple sclerosis, acute pain, chronic pain, epilepsy, drug-induced optic neuritis, peripheral neuropathy, myelopathy, ischaemic retinopathy, and glaucoma.

* * * * *